(12) United States Patent
Kim et al.

(10) Patent No.: US 9,514,549 B2
(45) Date of Patent: Dec. 6, 2016

(54) METHOD FOR REDUCING METAL ARTIFACT IN COMPUTED TOMOGRAPHY

(71) Applicant: Institute for Basic Science, Daejeon (KR)

(72) Inventors: Sung Whan Kim, Daejeon (KR); Ki Wan Jeon, Daejeon (KR); Chi Young Ahn, Daejeon (KR)

(73) Assignee: INSTITUTE FOR BASIC SCIENCE, Daejeon (KR)

( * ) Notice: Subject to any disclaimer, the term of this patent is extended or adjusted under 35 U.S.C. 154(b) by 0 days.

(21) Appl. No.: 14/748,935

(22) Filed: Jun. 24, 2015

(65) Prior Publication Data
US 2016/0125625 A1 May 5, 2016

(30) Foreign Application Priority Data
Oct. 30, 2014 (KR) .................. 10-2014-0148888

(51) Int. Cl.
| | | |
|---|---|---|
| G06K 9/00 | (2006.01) | |
| G06T 11/00 | (2006.01) | |
| A61B 6/03 | (2006.01) | |
| A61B 6/00 | (2006.01) | |

(Continued)

(52) U.S. Cl.
CPC .............. *G06T 11/003* (2013.01); *A61B 6/032* (2013.01); *A61B 6/5205* (2013.01); *A61B 6/5258* (2013.01); *A61B 6/5264* (2013.01); *G06T 5/001* (2013.01); *G06T 7/0012* (2013.01); *G06T 2207/10081* (2013.01); *G06T 2207/30004* (2013.01); *G06T 2210/41* (2013.01); *G06T 2211/421* (2013.01)

(58) Field of Classification Search
None
See application file for complete search history.

(56) References Cited

U.S. PATENT DOCUMENTS

2006/0285737 A1* 12/2006 Hamill ................ G06T 11/008
382/131
2008/0152203 A1* 6/2008 Bal ...................... G06T 11/008
382/131

(Continued)

OTHER PUBLICATIONS

Oehler, May, et al. "Evaluation of surrogate data quality in sinogram-based CT metal-artifact reduction." Optical Engineering+Applications. International Society for Optics and Photonics, 2008. APA.*

(Continued)

*Primary Examiner* — Shefali Goradia
(74) *Attorney, Agent, or Firm* — John P. White; Cooper & Dunham LLP

(57) ABSTRACT

A method for reducing metal artifacts in computed tomography (CT) is disclosed. The method for reducing metal artifacts in CT includes: obtaining a sinogram reduced in size from an original sinogram; setting up a linear algebraic equation according to remaining data excluding data damaged by a metal based on the obtained sinogram; restoring a low-resolution image based on the set up linear algebraic equation; calculating a sinogram from the restored low-resolution image; restoring a sinogram by disposing the calculated sinogram data in the original sinogram and by utilizing the calculated sinogram data as pre-information; and restoring a final CT image from the restored sinogram. Through introduction of a novel metal artifact reduction (MAR) technique referred to as an algebraic correction technique (ACT) using an intermediate image of an attenuation coefficient of an outside of a metal area, an image closest to an original image can be obtained by minimizing metal artifacts in CT.

6 Claims, 4 Drawing Sheets

(51) Int. Cl.
*G06T 7/00* (2006.01)
*G06T 5/00* (2006.01)

(56) References Cited

U.S. PATENT DOCUMENTS

2008/0165920 A1* 7/2008 De Man ............... A61B 6/5282
378/17
2010/0183214 A1* 7/2010 McCollough ......... A61B 6/032
382/131

OTHER PUBLICATIONS

Gu, Jianwei, et al. "Metal artifacts reduction in CT images through Euler's elastica and curvature based sinogram inpainting." Proc. SPIE. vol. 6144. 2006.*

Jeon, K. et al. (2014). Algebraic correction for metal artifact reduction in computed tomography. *J. KSIAM*, 18(2), 157-166.

* cited by examiner

METHOD FOR REDUCING METAL ARTIFACT IN COMPUTED TOMOGRAPHY

CROSS-REFERENCE TO RELATED APPLICATIONS

This application claims priority of Korean Patent Application No. 10-2014-0148888, filed Oct. 30, 2014, the contents of which is hereby incorporated by reference in its entirety.

BACKGROUND

1. Technical Field

The present invention relates to a method for reducing metal artifacts in computed tomography (CT), and more particularly, to a method for reducing metal artifacts in CT, which restores an original image of an area generated by a metal in an X-ray sinogram by extracting pre-information from an image restored to a small size.

2. Description of the Related Art

Computed tomography (CT) provides 2-dimensional and 3-dimensional high-resolution tomographic images of a human body from a measured X-ray projection image.

Although there is a controversy over dangers related to exposure to X-ray emission, CT has been widely used for the purpose of diagnosis and treatment as a powerful tool for investigating an inside of the human body and as various medical imaging techniques for disease. A metal object transplanted into the human body can cause serious side effects in a CT image and can deteriorate quality of a reconstructed CT image.

Generally, metals strongly attenuate an X-ray beam and measured attenuation of the metal given X-ray beam on the detector suffer from severe photon starvation. Thus, after-image projection data becomes inaccurate.

Metal artifact reduction (MAR) for improving quality of the CT image is one issue of CT application in clinical practice, and several MAR algorithms have been proposed over the past 30 years. R. M. Lewitt and R. H. T. Bates developed the first MAR image reconstruction method using an incomplete projection image (R. M. Lewitt and R. H. T. Bates 1978 Image reconstruction from projections: IV: Projection completion methods (computational examples), Optik 50, pp. 269-278). Here, projection measurement through metal is presumed to be omitted and is restored by polynomial interpolation. In addition to linear and polynomial interpolation, wavelet interpolation, sinogram interpolation and normalized MAR interpolation techniques have been proposed to fill the omitted projection data. These MAR algorithms can be classified into projection and sinogram completion methods. Over the last 10 years, iterative methods of modeling a physical phenomenon of metal artifacts have established another class of MAR algorithm, wherein noise and beam hardening are modeled. As compared with the projection completion methods, model-based iterative methods are computationally intensive and have a limitation in clinical application.

In the projection completion method, omitted projections for a metal trace can be filled by seriating flow of undamaged projections adjoining the metal trace using various restoration algorithms such as interpolation and total variation. Such typical methods, in which gaps of the omitted projections for an area of the metal trace in a sinogram are filled with the undamaged projections, can distort an attenuation coefficient outside the metal object.

FIGS. 1(a), 1(b) and 1(c) show a phantom model including two metals placed in a white area, a sinogram thereof, and a sinogram area in which a projection passing through a red point corresponds to an angle range surrounded by a metal area, respectively. As the point approaches the metal area, the angle, range, in which the projection passing through the point is disturbed by the metal, becomes larger. Therefore, existing filling methods can cause inaccurate information on the projections passing through the red point. As a result, a CT image reconstructed from such a corrected sinogram by a filtered back projection (FBP) method can be less efficient in restoring details of a true image of the phantom model. Efficiency of the projection completion method has a high dependency on accuracy of synthesized data.

FIG. 1 (a) shows the phantom model including the two metals placed in the white area, and FIG. 1 (b) is the sinogram thereof. Blue and red curves in FIG. 1 (b) show traces of projections passing through blue and red points placed outside the metal area in FIG. 1 (a), respectively. FIG. 1 (c) shows a zoomed-in image of an area surrounded by a box in FIG. 1 (b). The projections passing through the red point are blocked in a projection angle range by the metal.

BRIEF SUMMARY

The present invention has been conceived in consideration of the problems as set forth above and is aimed at providing a method for reducing metal artifacts in computed tomography (CT), which enables an image closest to an original image to be obtained by minimizing metal artifacts in CT through introduction of a novel metal artifact reduction (MAR) technique referred to as an algebraic correction technique (ACT) using an intermediate image of an attenuation coefficient of an outside of a metal area.

In accordance with one aspect of the present invention, a method for reducing metal artifacts in CT includes:

a) obtaining a sinogram reduced in size from an original sinogram;

b) setting up a linear algebraic equation according to remaining data excluding data damaged by a metal based on the obtained sinogram;

c) restoring a low-resolution image based on the set up linear algebraic equation;

d) calculating a sinogram from the restored low-resolution image;

e) restoring a sinogram by disposing the calculated sinogram data in the original sinogram and by utilizing the calculated sinogram data as pre-information; and f) restoring a final CT image from the restored sinogram.

Here, in operation a), the original sinogram is reduced in size in a direction in which a detector is placed.

In addition, in operation c), the low-resolution image may be restored using Tikhonov regularization.

Further, after restoration is performed in operation e), the method may further include calculating a metal area.

Furthermore, in restoring the final CT image in operation f), the method may further include performing interpolation by reflecting data for the calculated metal area.

According to the present invention, through introduction of the novel metal artifact reduction (MAR) technique referred to as the algebraic correction technique (ACT) using the intermediate image of the attenuation coefficient of the outside of the metal area, the image closest to the original image can be obtained by minimizing metal artifacts in CT.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Prior to a detailed description of embodiments of the present invention, it is assumed that an image processing system (for example, computer system), which can be provided with CT image data scanned in a CT scanner and can process the provided CT image data, is established to realize a method according to the present invention. In addition, such an image processing system (computer system) includes: a controller provided with a processor processing image data or information; a display configured to display data (information) input from the outside and a result processed by the controller; and a memory storing data processed by the controller and various applications necessary for operation of the image processing system (computer system).

Hereinafter, embodiments of the present invention will be described in detail with reference to the accompanying drawings.

Figure 2:
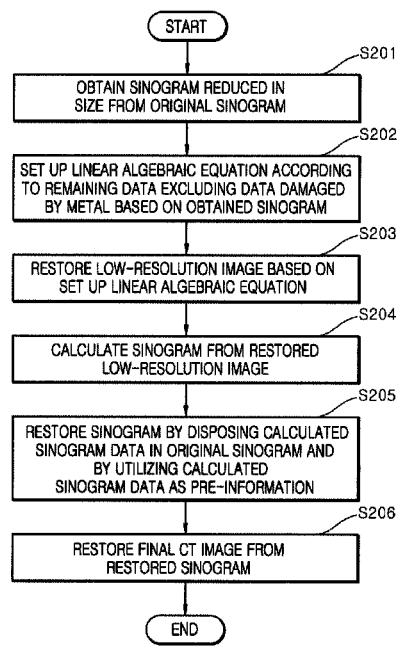
FIG. 2 is a flowchart of a method for reducing metal artifacts in CT according to one embodiment of the present invention.

FIG. 2 is a flowchart showing processes of performing a method for reducing metal artifacts in CT according to one embodiment of the present invention.

Referring to FIG. 2, in a method for reducing metal artifacts in CT according to the present invention, an original sinogram according to CT image data scanned by a CT scanner is provided first to a controller of an image processing system (or computer system, not shown). Then, the controller processes the original sinogram to obtain a sinogram reduced in size from the original sinogram (S201). Here, the original sinogram is reduced in size in a direction in which a detector is placed. That is, an image reduced in size from the original sinogram in the direction, in which the detector is placed to detect projection light of X-rays irradiated for CT, is obtained. This process reduces sizes of matrices and unknown quantities which are used in generating an intermediate image. Through this process, calculation can be quickly performed by reducing the number of unknown quantities of a linear equation to be solved.

As such, if the sinogram reduced in size (reduced in a relatively small ratio) from the original sinogram is obtained, the controller sets up a linear algebraic equation according to remaining data excluding data damaged by a metal based on the obtained sinogram (S202).

Here, the linear algebraic equation may be represented by the following equation:

$$\sum_{j=1}^{N} w_{ij} f_j = p_i, i = 1, 2, \ldots, M$$

where M is the number of projection measurement objects; N is the number of grids; $w_{ij}$ is a weighting coefficient equal to a fragmentary length or area of a j-th image pixel intercepted by an i-th ray; and $p_i$ is measured projection data having M pixels.

Here, since only a small number of image pixels contribute to a certain projection and a matrix W ($W=(w_{ij})$) has a sparse density, it is considered that most of the weighting, coefficients ($w_{ij}$) are 0 (zero). The above equation will be described again below.

As such, if setting up of the linear algebraic equation is completed, the controller restores a low-resolution image based on the set up linear algebraic equation (S203). Here, the low-resolution image may be restored using Tikhonov regularization.

If restoration of the low-resolution image is completed, the controller calculates a sinogram from the restored low-resolution image (S204). In addition, the sinogram is restored by disposing the calculated sinogram data in the original sinogram and by utilizing the calculated sinogram data as pre-information (S205). Here, after restoration is performed, the method may further include calculating a metal area by the controller.

Then, if restoration of the sinogram is completed, the controller restores a final CT image from the restored sinogram (S206). Here, in restoration of the final CT image, the method may further include performing interpolation in consideration of data for the calculated metal area.

Hereinafter, additional detailed descriptions of the method for reducing metal artifacts in CT according to the present invention will be provided.

The method for reducing metal artifacts in CT according to the present invention solves problems in an algebraic reconstruction technique (ART) described below. Therefore, the algebraic reconstruction technique will be described first.

<Algebraic Reconstruction Technique (ART)>

The algebraic reconstruction technique can result in an iterative technique and was first applied to computed tomography (CT). In the algebraic reconstruction technique, it is assumed that a certain reconstructed area (for example, a rectangle or circle) is known and that the area includes all scanned objects. Here, the area is divided into quadrangular grids, and there is the following linear relation between measured projection data (P) having M pixels and an unknown image (f) having N pixels.

$$\sum_{j=1}^{N} w_{ij} f_j = p_i, i = 1, 2, \ldots, M \qquad \text{[Equation 1]}$$

where M is the number of projection measurement objects; N is the number of grids; and $w_{ij}$ is a weighting coefficient equal to a fragmentary length or area of a j-th image pixel intercepted by an i-th ray.

Here, since only a small number of image pixels contribute to a certain projection and a matrix W ($W=(w_{ij})$) has a sparse density, most of the weighting coefficients ($w_{ij}$) are 0 (zero). An iterative algorithm for solving the linear system of Equation 1 may be represented by the following equation.

$$f^{(i)} = f^{(i-1)} - \frac{<f^{(i-1)}, w_i> - p_i}{<w_i, w_i>} w_i, i = 1, 2, \ldots, M \quad \text{[Equation 2]}$$

where $<*,*>$ is a dot product in a space $R^N$; $w_i=(w_{i1}, w_{i2}, \ldots, w_{iN}) \in R^N$; and $f^{(i)}$ is an orthogonal projection of $f^{(i-1)}$ onto a hyperplane $<f, w_i> = p_i$.

Equation 2 is based on consideration of a solution f as one point in $R^N$ which is a cross-point of M hyperplanes. However, since N is sometimes much larger than M, the linear system of Equation 1 provides only an insufficient decision. More seriously, projections obtained from CT often include noise which causes P not to be placed within a range of an operator W. Even though convergence is ensured, Equation 2 will slowly converge upon a solution.

<Algebraic Correction Technique (ACT) for MAR>

Figure 3:
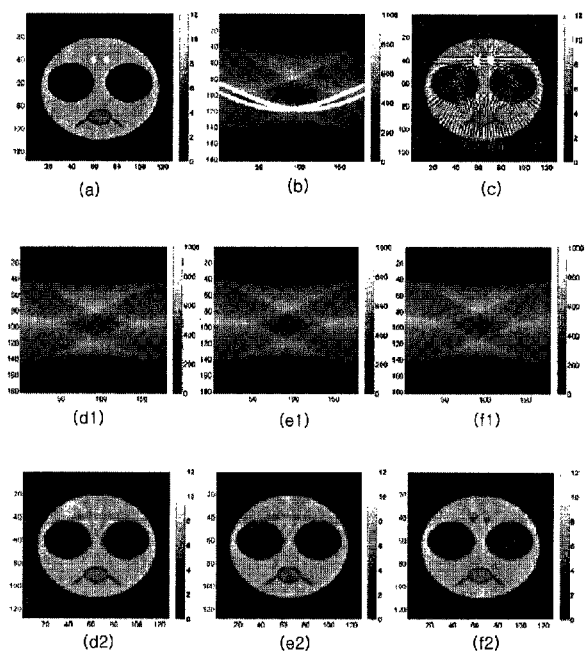
FIG. 3 shows processes of obtaining a final reconstructed image from an initial image including a metal area through correction using an ACT used in the method according to the present invention.

FIG. 3 shows processes of obtaining a final reconstructed image from an initial image including a metal area through correction using an ACT used in the method according to the present invention Referring to FIG. 3, FIG. 3 (a) shows a phantom model including two metal areas transplanted into a white area and several areas having different attenuation values, and FIG. 3 (b) shows a sinogram of the phantom model. Filtered back projection (FBP) creates an image having a streak (long line shape having a different color from a portion forming a background) side effect caused by a metal object as shown in FIG. 3 (c). Through simple boundary determination, the metal area in the reconstructed image may be determined. Then, damaged projections are cut out of a sinogram in which a ray is placed on the metal area. Using restoration methods such as total variation and harmonic inpainting restoration methods, omitted projections may be filled. As a result, FBP provides an improved image without the streak side effect from a synthesized sinogram. FIG. 3 (d1) is a sinogram filled by the harmonic inpainting restoration method and FIG. 3 (d2) is a FBP image thereof. In addition, FIG. 3 (e1) is a sinogram filled by the total variation method and FIG. 3 (e2) is a FBP image thereof.

It can be seen that reconstructed images of FIGS. 3 (d2) and 3 (e2) are extremely improved as compared with a reconstructed image of FIG. 3 (c). However, in FIGS. 3 (d2) and 3 (e2), it is difficult to distinguish two small circular areas which were initially disposed on the metal area. The reason is as follows.

Figure 1:
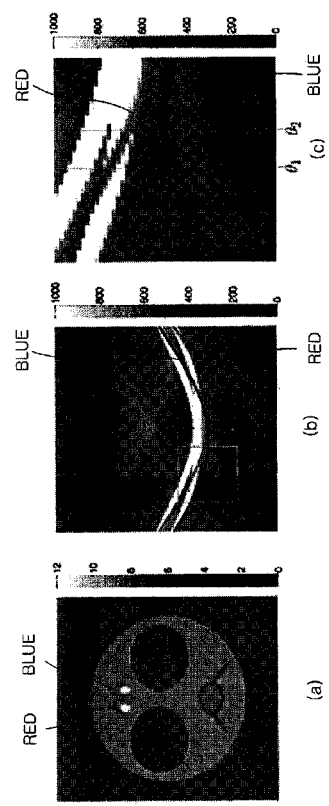
FIG. 1 shows a phantom model including two metals disposed in a white area, a sinogram thereof, and a zoomed-in image of a specific portion of a sinogram area.

First, "$r_0$" is assumed to be one point (for example, a red point in FIG. 1 (a)) in a circular area. The red curve in FIG. 1 (b) traces projections in which a ray passes through the point "$r_0$". FIG. 1 (c) (zoomed-in image of an area surrounded by a box in FIG. 1 (b)) shows a blind part of attenuation information of the red point "$r_0$". In other words, since projection light passing through the point "$r_0$" at a projection angle ranging from $\theta_1$ to $\theta_2$ is blocked by the metal object, there is no projection including attenuation information at "$r_0$" on an angle area $[\theta_1, \theta_2]$. Therefore, since a typical method, in which the omitted projections in the box are filled using neighboring undamaged data, can neglect information on an attenuation value at the point "$r_0$", a CT image reconstructed from such a manipulated sinogram by FBP is less efficient in restoring details of a true image of an attenuation coefficient of the phantom model.

Therefore, according to the present invention, another approach for filling a metal trace in a sinogram is adopted. That is, according to the present invention, an intermediate image of an attenuation coefficient reconstructed from incomplete projection data is used instead of using a boundary projection of the metal trace.

First, M is assumed to be the number of projection data measured for all projection angles, and P ($P=(p_1, p_2, \ldots, p_M) \in R^M$) is assumed to be measured projection data. In addition, a projection object $p_k$ is divided into two portions, that is, a damaged portion and an undamaged portion. Further, $P_t$ ($P_t=(p_{t1}, \ldots, p_{tm1}) \in R^{m1}$) is assumed to be a vector of an undamaged projection object in which a ray is not in contact with the metal object, and $P_s$ ($P_s=(p_{s1}, \ldots, p_{sm2}) \in R^{m2}$) is assumed to be a vector of a damaged projection object in which a ray passes through the metal object. Here, $m_1+m_2=M$ is assumed. In a lot of clinical practices, the measurement number M is huge. Even though the damaged data $P_s$ is removed from the overall data P, since $m_1$ is still large, application of the method according to the present invention, that is, application of Equation 2 conflicts with a memory limit. Thus, considerable calculation time is required. Therefore, according to the present invention, a sparse quadrangular grid $D_i$ (i=1, 2, . . . , N) having a wider width ($\delta$) than a size of a detector is used, and f (f=($f_1, f_2, \ldots f_N$)$\in R^N$) is assumed to be an image vector. If a cross-area of $D_i$ and the metal area are larger than $\delta^2/2$, an image value $f_i$ is assumed to be 0 (zero). Here, although there are several methods for creating a linear system (that is, Equation 1) having various sizes, it is advantageous that the created linear system is not large. Therefore, according to the present invention, it is proposed that N undamaged projection objects $p_{tk}$ be selected from $P_t$ and, as a result, the N undamaged projection objects $p_{tk}$ are uniformly distributed in terms of a degree of a term through components of $P_t$. $\tilde{p}_t \in R^N$ in which components thereof are the undamaged projection objects $p_{tk}$ as selected above is assumed to be one vector. Then, a matrix form of the linear system (Equation 1) may be obtained as the following equation.

$$Wf = \tilde{p}_t \quad \text{[Equation 3]}$$

Here, since a weighting matrix W is not large, the iterative method of Equation 2 or modifications thereof are applied. To solve Equation 3, a well-known least squares method provided with Tikhonov regularization is defined as follows.

$$\arg\min_f (\|Wf - \tilde{p}_t\|_2^2 + \alpha \|f\|_2^2) \quad \text{[Equation 4]}$$

where $\alpha$ is a regularization parameter. Here, Equation 4 has a unique solution as follows.

$$f = (W^T W + \alpha I)^{-1} W^T \tilde{p}_t \quad \text{[Equation 5]}$$

where $I \in R^{N \times N}$ is a unit matrix.

In Equation 5, the solution f is a temporary image of an attenuation coefficient on the sparse grid $D_i$. Sporadic projection data is synthesized from the image f and the synthesized projection data is interpolated into a metal trace in a sinogram in order to replace the damaged data $p_s$.

Eventually, according to the present invention, FBP is applied to obtain a final reconstructed image from such an updated sinogram.

<Summary of Method According to Present Invention>

Unlike the typical restoration methods using boundary data of the metal trace, the aforementioned algebraic correction technique (ACT) used in the method according to the present invention uses the intermediate image of the attenuation coefficient as pre-information for metal artifact reduction (MAR). Briefly, the ACT is based on the following operations.

Operation 1: Restoring a filtered back projection (FBP) image from measured projection data.

Operation 2: Finding an image of a metal area from a reconstructed image using a simple reference point and cutting out a metal trace from a sinogram.

Operation 3: Dividing a vector p into two vectors, $p_s$ (projections in which components thereof are damaged by a metal object) and $p_t$ (undamaged projections in which components thereof are outside of the metal trace).

Operation 4: Dividing a phantom model into sparse quadrangular grids ($D_{i,i}$=1, 2, . . . , N), uniformly selecting N undamaged projections from $p_t$, and assuming $\tilde{p}_t$ as a vector of the N selected projections.

Operation 5: Finding a solution f as defined in Equation 5. If an intersection area of $D_i$ and the metal area is larger than ½ of a $D_i$ area, an image value $f_i$ is assumed to be 0 (zero).

Operation 6: Applying the solution f to the metal trace.

Operation 7: Interpolating a projection of f applied to the metal trace in order to replace $p_s$.

Operation 8: Reconstructing a final image from an updated sinogram using FBP.

Figure 4:
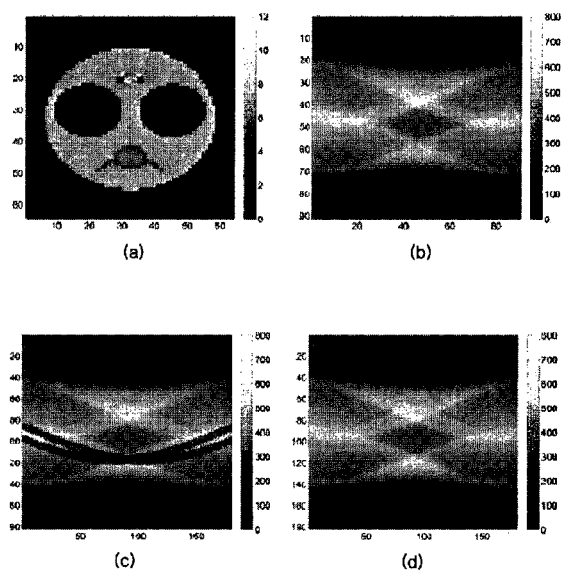
FIG. 4 shows a procedure of correction from an intermediate image obtained by application of a least squares method provided with Tikhonov regularization used in the method according to the present invention.

FIG. 4 (a) shows an intermediate image obtained by solving a minimization problem (see Equation 4) on a sparse grid. Obviously, it can be seen that a reconstruction result is less influenced by metal side effects. According to the present invention, forward projection is performed to obtain pre-information for sinogram correction (see FIG. 4 (b)) from the obtained image. FIG. 4 (c) shows operation of correction based on information that the size of a fine grid is two times that of the sparse grid. According to the present invention, projection data of the sparse grid is placed at the same point as that of the fine grid in a metal trace area. Then, as in FIG. 4 (d), harmony restoration is applied to fill a point remaining in the metal trace area. FIG. 3 (f2) is a final result obtained by applying FBP to FIG. 3 (f1) based on the processes as described above.

As described above, advantageously, the method for reducing metal artifacts in CT according to the present invention can allow an image closest to an original image to be obtained by minimizing metal artifacts in CT through introduction of a novel metal artifact reduction (MAR) technique referred to as an algebraic correction technique (ACT) using an intermediate image of an attenuation coefficient of the outside of the metal area.

Although the present invention has been described with reference to some embodiments in conjunction with the accompanying drawings, it should be understood that these embodiments are provided for illustration only and that various modifications and other equivalent embodiments can be made without departing from the spirit and the scope of the present invention. Thus, the scope of the present invention should be determined by the attached claims.

What is claimed is:

1. A method for reducing metal artifacts in computed tomography (CT), comprising:
    a) obtaining a sinogram reduced in size from an original sinogram;
    b) setting up a linear algebraic equation according to remaining data excluding data damaged by a metal based on the obtained sinogram;
    c) restoring a low-resolution image based on the set up linear algebraic equation;
    d) calculating a sinogram from the restored low-resolution image;
    e) restoring a sinogram by disposing the calculated sinogram data in the original sinogram and by utilizing the calculated sinogram data as pre-information; and
    f) restoring a final CT image from the restored sinogram.

2. The method according to claim 1, wherein, in operation a), the original sinogram is reduced in size in a direction in which a detector is placed.

3. The method according to claim 1, wherein, in operation b), the linear algebraic equation is represented by the following equation:

$$\sum_{j=1}^{N} w_{ij} f_j = p_i, i = 1, 2, \ldots, M$$

where M is the number of projection measurement objects; N is the number of grids; $w_{ij}$ is a weighting coefficient equal to a fragmentary length or area of a j-th image pixel intercepted by an i-th ray; and $p_i$ is measured projection data having M pixels.

4. The method according to claim 1, wherein, in operation c), the low-resolution image is restored using Tikhonov regularization.

5. The method according to claim 1, further comprising: calculating a metal area after restoration is performed in operation e).

6. The method according to claim 5, further comprising: performing interpolation by reflecting data for the calculated metal area in restoring the final CT image in operation f).

* * * * *